United States Patent [19]
Schader et al.

[11] Patent Number: 5,889,257
[45] Date of Patent: Mar. 30, 1999

[54] HEATED DENTAL KNIFE

[75] Inventors: Harry W. Schader, Sand Point, Id.;
Charles L. Bull, Osage Beach, Mo.

[73] Assignee: Challenge Products, Inc., Osage Beach, Mo.

[21] Appl. No.: 78,242

[22] Filed: May 13, 1998

[51] Int. Cl.⁶ .................................................. H05B 1/00
[52] U.S. Cl. .................... 219/229; 219/227; 219/228; 219/229; 219/238; 219/240; 30/140
[58] Field of Search .................... 219/227–231, 219/233, 236, 238, 240; 228/51, 55; 606/28–31; 30/140, 353, 335, 356

[56] References Cited

U.S. PATENT DOCUMENTS

| | | | |
|---|---|---|---|
| 1,580,841 | 4/1926 | Mackler | 69/20 |
| 1,584,392 | 5/1926 | Markle | 30/140 |
| 1,772,616 | 2/1930 | Ruhl | 219/239 |
| 2,589,509 | 3/1952 | Petraglia | 126/413 |
| 2,646,494 | 7/1953 | Fegan | 83/171 |
| 3,017,487 | 1/1962 | Priestly | 83/171 |
| 3,297,856 | 1/1967 | Gershon | 219/233 |
| 3,524,045 | 8/1970 | Siegel | 219/229 |
| 4,208,571 | 6/1980 | Moumaneix et al. | 219/227 |
| 4,209,017 | 6/1980 | Shaw | 606/28 |
| 4,238,664 | 12/1980 | Anderson | 219/230 |
| 4,401,616 | 8/1983 | Wagner | 264/138 |
| 4,539,467 | 9/1985 | Wenger | 219/233 |
| 4,602,144 | 7/1986 | Vogel | 219/230 |
| 4,621,251 | 11/1986 | Keefe | 338/302 |
| 4,734,559 | 3/1988 | Fortune et al. | 219/241 |
| 4,924,067 | 5/1990 | Wilhelmson | 219/241 |
| 5,046,251 | 9/1991 | Scott | 30/140 |
| 5,059,769 | 10/1991 | Fortune | 219/238 |
| 5,117,091 | 5/1992 | Ely | 219/236 |
| 5,122,637 | 6/1992 | Bottorff et al. | 219/241 |
| 5,163,600 | 11/1992 | Barbarich et al. | 228/51 |
| 5,438,758 | 8/1995 | Roth-White | 30/140 |
| 5,446,262 | 8/1995 | McCambridge | 219/237 |
| 5,459,298 | 10/1995 | Tschakaloff | 219/227 |
| 5,565,122 | 10/1996 | Zinnbauer et al. | 219/227 |
| 5,611,798 | 3/1997 | Eggers | 606/31 |
| 5,683,603 | 11/1997 | Fortune | 219/229 |

*Primary Examiner*—Teresa Walberg
*Assistant Examiner*—Vinod D. Patel
*Attorney, Agent, or Firm*—Herzog, Crebs & McGhee, LLP

[57] ABSTRACT

A heated dental knife for trimming thermoplastic dental trays which has a heat sink temperature stabilizer and heating element designed to maintain a pre-selected blade temperature without adjustments under normal use in cutting such dental trays.

11 Claims, 3 Drawing Sheets

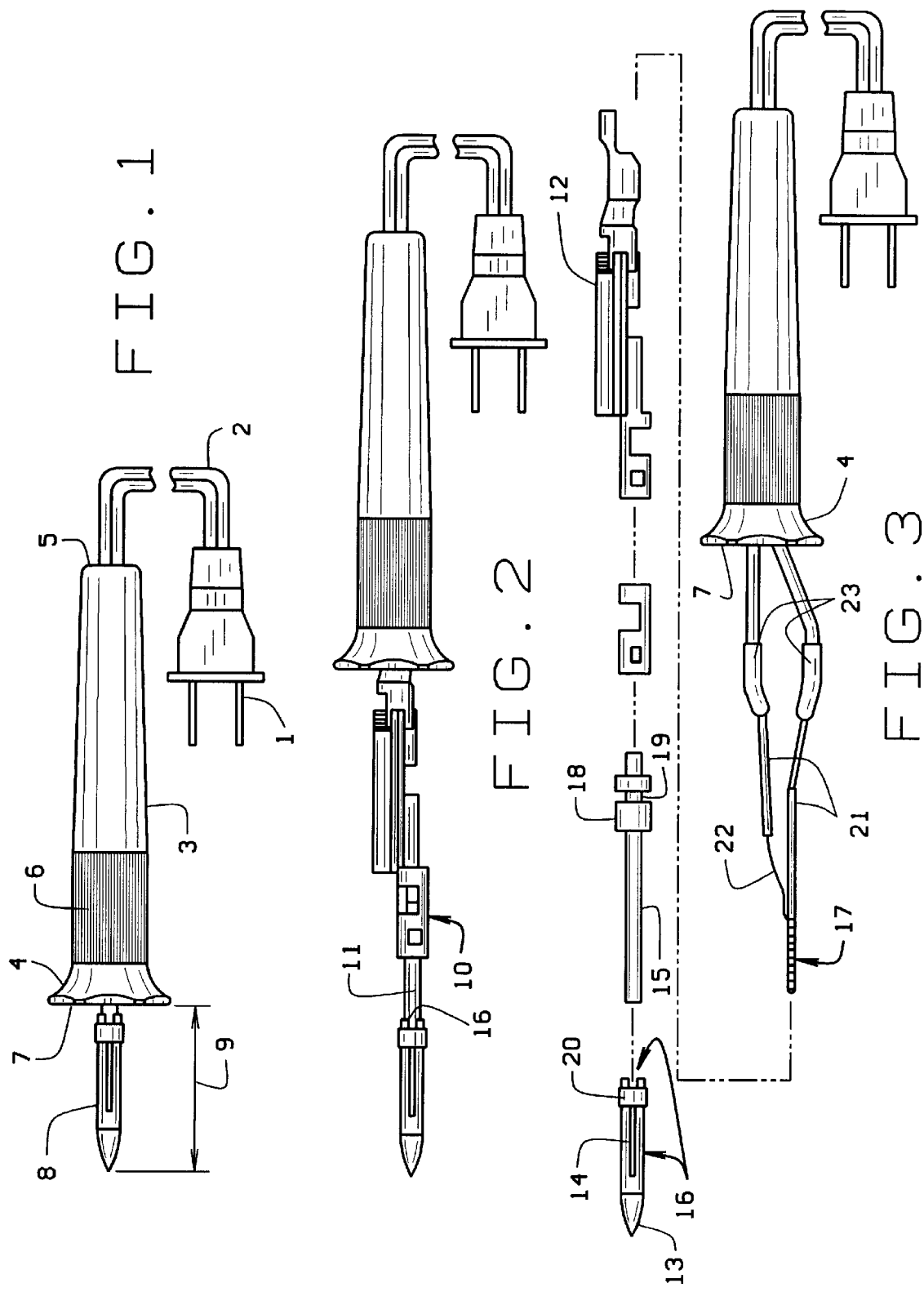

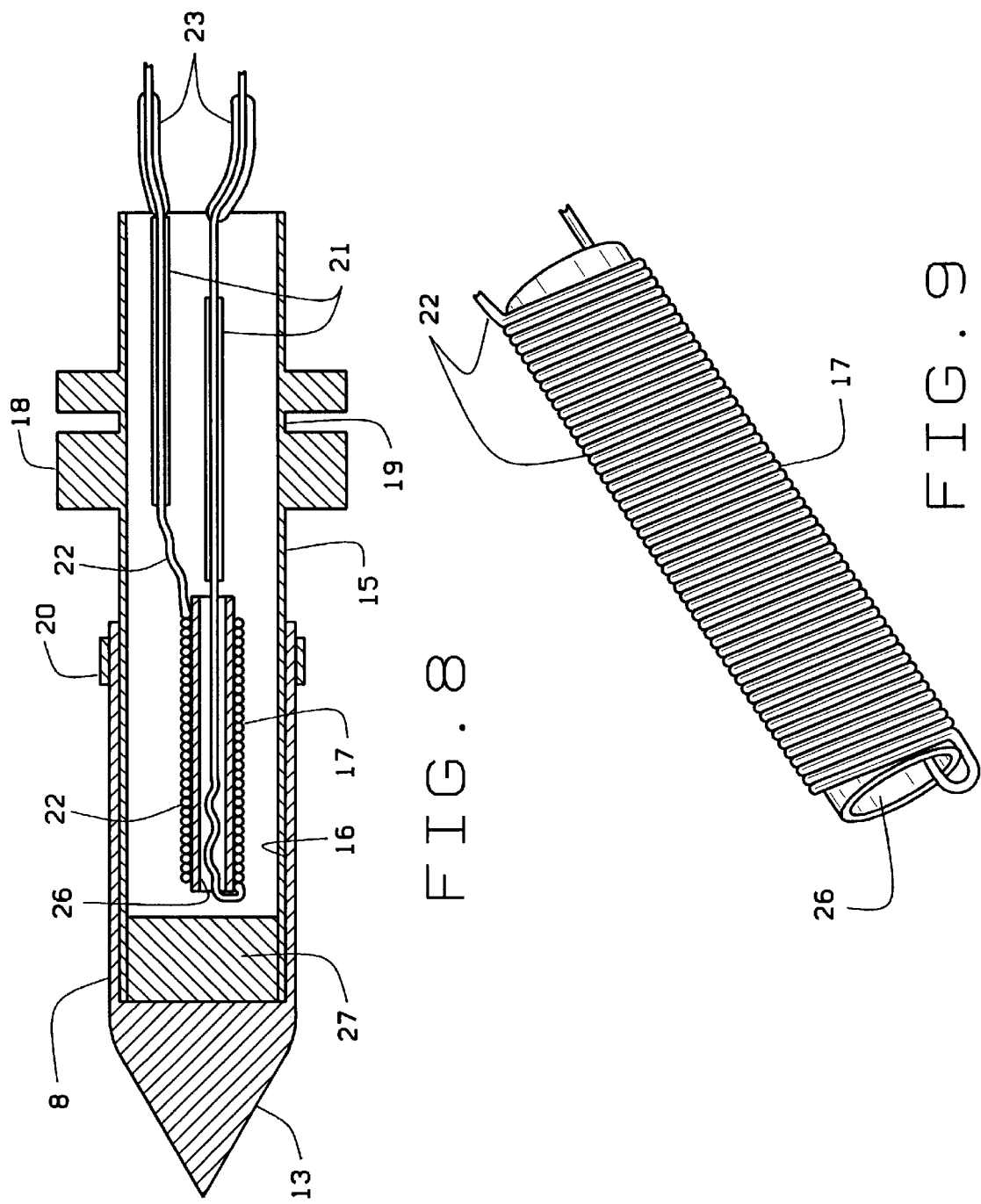

HEATED DENTAL KNIFE

BACKGROUND OF THE INVENTION

1. Field of the Invention

This invention relates to the field of dentistry and particularly dental knives for trimming thermoplastic dental trays.

2. Related Art

Thermoplastic dental trays are used in the application of dental fluoride, dental bleaching, and other like dental treatments. The dental tray is sometimes vacuum formed on a full size model of a patient's jaw ridge, which is the ridge-formed by parts of the gums, the adjacent teeth and the alveolar portions of the jaws, in the areas to receive the dental treatment. A mold of soft plastic material which hardens into such a full size model is obtained by taking an impression of the appropriate area of the patient's jaw ridge. The appearance and the fit of the finished dental tray depends to a large degree on the precision of the model on which the tray is formed and subsequently depends on the precision of the method of trimming the tray. The initial dental impression tray that is used to make the full size model is usually formed from a thermoplastic sheet. The initial impression tray closely approximates the shape of and size of the specific patient's jaw ridge for use as a mold in the manufacture of an accurate full size study model on which a more precise and final dental tray can be formed for use in a dental treatment. The creation, by vacuum forming, of a final hardened thermoplastic dental tray to be used for the fluoride, bleaching or other dental treatment requires trimming of the excess thermoplastic from the dental tray material to produce a tray with the desired shape to match the patient's gingival line. A trimming of the dental tray that matches the gingival line should produce a tray with a scalloped edge that matches the gingival line. Trimming or cutting is typically accomplished by using scissors with curved shear blades. However, there is a problem with a scissors trimming method. This method of trimming or cutting with scissors can only be done after the tray is removed from the mold and thus is very inaccurate. Once the tray is removed from the full size model, one must trim the tray utilizing the trace lines that remain as an impression from the model. There is great difficulty when scissors are used to accurately trim along the trace line impression left by the gingival line of the model in order to obtain the final tray to be used for application of the dental treatment. An additional problem is the difficulty in trimming the material with scissors once the material has fully cooled and hardened. The thermoplastic is substantially tough at body or room temperatures. Therefore when cut with scissors, the thermoplastic may stretch due to the shearing action of the scissors and this stretching may result in an oversize or misshapen dental tray. The accuracy of the trimming is key to the effective manufacture of a good dental tray for application of a fluoride or bleaching dental treatment. An accurate trimming process produces a dental tray that will have a tight and snug fit around the teeth to be treated. A tight and snug fit is desired for the most effective treatment. A dental tray that closely follows the shape of the patients gum line, 1 mil shy of gingival line, is desirable for the snug fit which promotes an effective treatment. When scissors are used, usually the distance between the gingival line and the dental tray is much greater than 1 mil and the tray thus overlaps the gum.

Also, trimming and cutting with scissors many times yield poor result such as a jagged edge which is not comfortable to the patient and many cuts or trims are not easy to accurately perform with scissors. Cutting with scissors is inherently a series of cuts, which may or may not align with each other. If not, a resulting jagged edge is probable. This result either makes for a jagged edge or loose fit or the tooth is not treated up to the gingival line.

Neither of the above results will provide an optimum treatment.

There are also heated dental knives that are utilized to trim thermoplastic dental trays. These heated knives have electrically powered heating elements that heat the blade tip. An adjustable heat setting is provided. The adjustable heat setting is usually provided by adjustment of a potentiometer which varies the voltage across a transformer and resulting power to the heating element. However, a problem with such heated dental knives is that there is no real time monitoring of the blade tip temperature, thus no feedback is provided for dynamic temperature control. There is only discrete voltage level adjustment capability. This type of heated knife will allow the actual blade cutting tip to over-shoot or under-shoot the optimal temperature if the potentiometer is set to the incorrect level. Adjusting the potentiometer to an optimal setting for trimming thermoplastic dental trays is accomplished by trial and error. Over-shooting the desired temperature will result in melting the thermoplastic. If melting occurs the thermoplastic will be deformed and possibly the severed thermoplastic will immediately meld back together after cutting. If under-shooting occurs the thermoplastic will possibly tear or cut unevenly instead of providing a cleanly seared cut. Temperature control at the blade tip is important because the heating element of dental knives such as the one described above are not designed to maintain a stable temperature range. For a given potentiometer setting, the temperature at the blade tip may vary widely. The ability to adjust the power level input to the heating element of the dental knife over a large temperature range is not needed or desired for the subject application because it allows more room for error. User error occurs when the level control is set to the wrong level. Also, there is a risk for error due to component anomalies such as failure of the potentiometer and failure the transformer assembly. In addition it is more difficult to design a dental knife that can maintain a stable temperature range at a given level setting when the power input to the heating element can be varied over a large range. There is not the ability to thermally design a dental knife that is optimized to maintain a temperature range for the fixed heating element power input and output needed for a dental tray knife.

Another difficulty with the current dental knives is that they are not ergonomically designed. Specifically the blade tip is too long for the comfortable application of trimming thermoplastic dental trays.

There are some prior art patents that address the forming, handling, or cutting of thermoplastic items. None are designed to perform the trimming or cutting of thermoplastic dental trays and none, if utilized, will yield the result of a dental tray that has a snug fit and closely follows the gingival line. For example, U.S. Pat. No. 5,046,251 issued Sep. 10, 1991 to Scott shows a portable lightweight tool employing a heating element and configured in a scissor-like embodiment whereby at least one blade of the scissors employs a heating element. A combination cutting and searing is achieved by the normal scissor-action of the embodiment. However, this item was designed to cut fabric material with high thermoplastic content and to be used by a seamstress, upholster, or the like. Scissors with one heated shear may make for ease of cutting, assuming the heating element achieves a high enough temperature to sear dental thermoplastic when the thickness is considered in comparison to that of fabric. However, as noted above, cutting dental trays with scissors makes jagged edges due to the discontinuance nature. Also, cutting with insufficient heat will result in tearing and stretching of the thermoplastic and with too much heat results in resealing of the cut. In addition, the scissors-like embodiment will not solve the problem for the trimming required in areas that are difficult to trim with scissors. A more practical solution to the continuing problem of jagged dental trays is needed.

SUMMARY OF INVENTION

It is in view of the above problems that the present invention was developed. The Applicant has taken a different approach than the above-cited patents. Applicant has recognized the real need to provide a simple, reliable trimming tool for smoothly cutting and trimming thermoplastic dental trays. The applicant has also recognized the non-obvious inherent problems when utilizing the conventional methods described above.

It is an object of the invention to economically provide a trimming and cutting tool for thermoplastic dental trays that provides an accurate temperature control for precision cutting including trimming and cutting in areas where conventional scissors are not effective.

It is a further object of the invention to provide a trimming tool that provides a cut with a smooth finish without leaving undesirable rough edges.

It is a further object of the invention to provide a tool that cuts thermoplastic with the assistance of heat sufficient to continuously sear without melting thus resulting in undesirable results.

It is further the object of the invention to provide automatic or inherently tight temperature control at the blade tip of the tool so that melting or tearing of the thermoplastic does not occur.

It is further the object of this invention to eliminate the variable adjustment capability and the errors and failure associated therewith.

It is further the object of the invention to provide adequate cutting edges and a tool designed with good ergonomics.

It is a further object of the invention to provide a cutting tool that shortens the time required to produce a dental tray.

These above objects are achieved by utilizing a heated dental knife that has a tapered double knife edge blade that transitions to a sharp point; a cutting tip portion of a blade, wherein the last ¼ distance of the blade, that tapers in thickness from about 3 mm to about 0.25 mm; a heating element and thermocouple device; a tight temperature control system adapted to maintain the temperature at the cutting blade from about 350 degrees Fahrenheit to about 450 degrees Fahrenheit without the need for a power level adjustment; and a blade that is a short distance from the handle for better ergonomics.

The invention thus provides an economical, safe, and low maintenance solution to solving the need for an accurate tool.

BRIEF DESCRIPTION OF THE DRAWINGS

The drawings include:

FIG. 1, an overall assembly diagram showing a preferred embodiment of the invention;

FIG. 2, a side view of the overall assembly showing the wire bracket, heating element and knife blade exploded outward;

FIG. 3, an exploded view providing an illustrated parts breakdown of the preferred embodiment of the overall assembly;

FIG. 8, a vertical longitudinal diametric cross section taken along Line 8—8 of FIG. 2; and FIG. 9, a detail of the area 9—9 of FIG. 3 which shows the resistive wire wound around a ceramic tube core.

DESCRIPTION OF THE PREFERRED EMBODIMENTS

Figure 4:
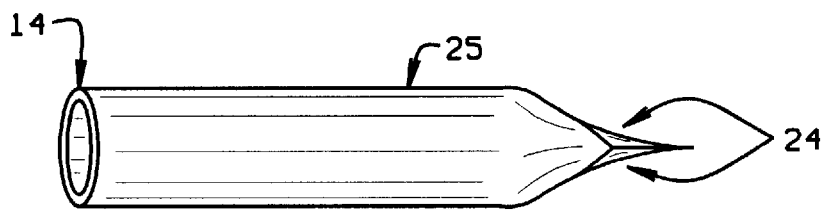
FIG. 4, a top view of the knife blade.

The invention is first described with reference to FIG. 1 which depicts the overall assembly. The detailed structure and function of the heated knife is then described with reference to FIGS. 1, 2, 3, 4, 5, 6, 7, 8 and 9.

Referring to FIG. 1, there is a standard plug 1 for a 60 Hz 110-volt electrical outlet that is electrically connected to a power cord 2 which is the power source for the assembly. Power cord 2 enters the rear end of handle 3 that houses a portion of the assembly. Handle 3 is made of hard plastic in its preferred embodiment. Handle 3 is cylindrical in shape with a hollowed interior that provides a cavity to house electrical components of the assembly. Handle 3 has a curved taper 4 for ease in handling. Handle 3 has its smallest diameter on the rear end 5 of the handle. The diameter of the handle 3 gradually increases from the rear end 5 of the handle to the blade end of the handle. The diameter remains constant for a short distance and then sharply flares to the blade end. This portion of handle 3 with constant diameter has a textured surface 6 for gripping purposes. The handle 3 transitions from the textured portion 6 to the sharply flared portion 4 of the cylindrical handle which diametrically increases rapidly to form the opening 7 from which a blade 8 extends. The blade 8 extends beyond the opening 7 a distance 9 which is from about 25 mm to about 60 mm. The distance 9 is an ergonomic consideration. An adequately short distance 9 allows a user of a heated knife with this preferred embodiment to better control the placement and the travel of the blade tip.

Referring to FIG. 2 a wire bracket/heating element assembly 10 is shown. A blade 8 is also shown installed on the assembly 10. Assembly 10 is normally housed within the internal cylindrical volume of handle 3, but is shown here as exploded outward. The blade 8 is installed by axially inserting the shaft 11 of the heating element assembly into the hollow female receptacle 16 of blade 8.

Referring to FIG. 3, an exploded view of an illustrated parts breakdown is shown. A blade 8 made of hardened metal, which is from about 25 mm to about 50 mm in total length, has a blade tip 13. Tip 13 extends for about ¼ of the total axial length and the receptacle 16 for about ¾ of the total axial length of the blade 8. Blade tip 13 is tapered forming a sharp chevron point. Point is a tapered chevron formed by opposing concave tapers and opposing angled tapers all culminating at a single point at the tip of the knife blade. The hollowed receptacle portion 16 of the blade body has axial expansion slits 14 on diametrically opposing sides of the hollowed cylindrical blade body forming the female receptacle that receives the heating element assembly enclosure tube shaft 11.

A heating element enclosure tube 15 made of stainless steel is shown which comprises the shaft 11 as shown in FIG. 2 and a heatsink 18. Tube 15 provides efficient transfer of heat from a heating element 17 within tube 15 to the hollow receptacle portion 16 of metallic blade by thermal conductivity. Wire bracket 12 is a two piece polycarbonate plastic holder for the power cord. Heating element enclosure tube 15 is also secured in bracket 12.

A heating element 17 is shown within enclosure tube 15. Heating element 17 is 0.33 mm diameter resistance wire 22 of a precise length and precisely wound around a ceramic tube core 26, see FIG. 9. The precise winding around a ceramic tube core 26 allows heating element 17 to maintain a constant temperature range. The precise design of the resistance wire winding around the ceramic tube is key to maintaining a constant temperature range. The resistance wire is wound around a ceramic tube with inner diameter of about 1 mm and outer diameter of about 2.2 mm. The resistance wire is wound around the ceramic tube. The stainless steel enclosure 15 is also critical to maintaining a constant temperature. Enclosure tube 15 is a stainless steel cylinder with a heat sink collar 18. The cylinder portion is open on one end for insertion of the heating element. The opening on the opposite end is a plug 27 of ceramic, see FIG. 8 material or other thermal insulation to prevent contamination of the tube. The inner diameter of the cylinder is 4.5 mm. The outer diameter of the cylinder is 5.1 mm. The collar 18 of enclosure 15 is stainless steel. The notched innermost outer diameter 19 of the heat sink collar is 5.12 mm. There is a stepped outermost outer diameter. The outermost diameter is 10 mm. The outer cylindrical wall of the collar is notched to form a stepped outer diameter of 6.15 mm. The heat sink collar of enclosure 15 is designed to act as a heat reservoir whose mass is sufficient to resist rapid heat transfer which would result in large temperature swings at the blade tip thereby greatly assisting in maintaining the desired temperature range. The heating element 17 is axially in thermal adjacency to thermally conductive enclosure 15 of the heating element 17. Enclosure 15 is axially inserted into the rear end hollowed cylindrical receptacle portion 16 of knife blade 8. The knife blade 8 is clamped to the heating element enclosure 15 with a metal band 20.

Insulation sleeving 21 insulates and protects the heating element 17 and its 0.03 mm wire 22 that leads from the power cord 2 connection to the winding of the heating element 17. Extruded tubing 23 is a heat shrink material that insulates and protects the connection between the heating element leads and the power cord. The heat shrinkable material can adequately insulate leads of different diameters that are connected. A flared portion 4 of the cylindrical handle 3 diametrically increases rapidly to form an opening 7 from which a blade 8 extends as shown.

Referring to FIG. 4, a top view of blade 8 is shown. The taper 24 of the blade tip from 3 mm to 0.25 mm is shown which provides a clean cut by quickly searing and adequately separating the thermoplastic material without melting back or causing jagged edges. Expansion slit 14 is shown which extends to 25.

Figure 5:
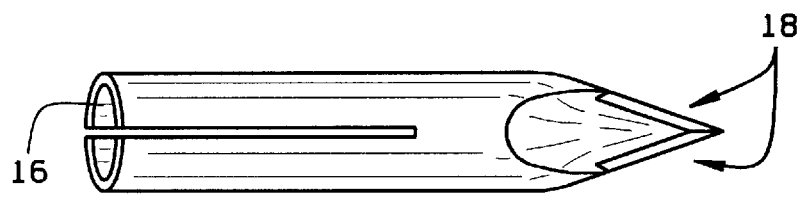
FIG. 5, a side view of the knife blade.

Referring to FIG. 5, a side view of blade 8 is shown. The double-edged blade tip 18 is shown.

Figure 6:
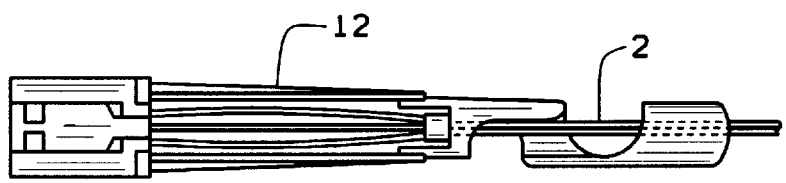
FIG. 6, a top view of the wire bracket.

Referring to FIG. 6, a polycarbonate plastic wire bracket 12 that holds the power cord 2 that threads through the plastic tubular like wire guide bracket 12 is shown. Tubular bracket 12 has portions of the shell cut away exposing the power cord 2. The cut away portion of the tubular bracket wall is not shown for illustration purposes. The bracket is actually built with a portion of the wall cut away as shown. The power cord 2 is electrically connected to a cable of the heating element 17 internal to the bracket 12.

Figure 7:
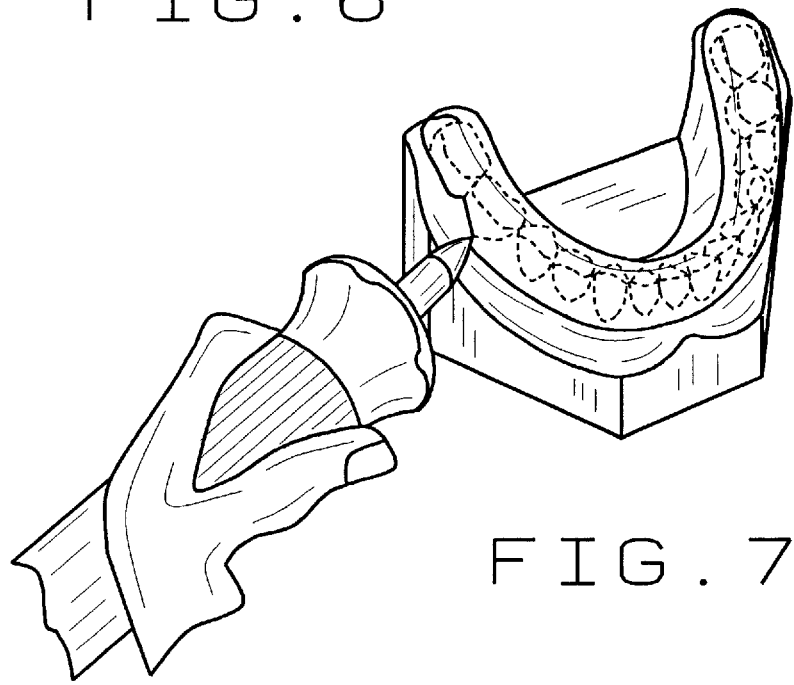
FIG. 7, Illustration of the tool being used to trim a thermoplastic dental tray from a thermoplastic sheet that has been formed on a full-scale model.

Referring to FIG. 7, the dental knife is shown in use.

Referring to FIG. 8, a cross section is shown of the heating element 17 co-axially inserted into the open end of the enclosure tube 15 with the associated ceramic tube core 26, resistive wire 22, wire insulation 21, and heat shrink 23. The enclosure tube 15 is closed on one end by a plug 27. The heat sink collar 18 is shown on the exterior circumferential surface of the enclosure tube. The enclosure tube is co-axially inserted into the hollow end 16 of the blade 8 which has a blade tip 13 and a metal band 20.

Referring to FIG. 9, a heating element 17 is shown with a ceramic tube core 26 and a resistive wire 22 circumferencially wound around said ceramic tube core.

In view of the foregoing, it is seen that the stated objects of the invention are achieved. The above description explains the principles of the invention and its practical application to thereby enable other skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description shall be interpreted as illustrative rather limiting. Thus, the breadth and scope of the present invention should not be limited by any of the above described exemplary embodiments, but should be defined in accordance with the following claims appended hereto and their equivalents.

The patents referenced herein are incorporated in their entirety for purposes of background information and additional enablement.

What is claimed is:

1. A heated dental knife for trimming thermoplastic dental trays comprising:

a spirally wound resistive wire heating element having a tubular ceramic cylindrical axial core;

a thermally conductive coaxial metal enclosure tube enclosing the heating element and in heat transfer adjacency to said heating element and with one end open receiving the heating element;

a heat sink temperature stabilizing coaxial metal body in heat transfer adjacency to said enclosure tube, adapted to receive heat from the heating element and enclosure tube and then to transfer the heat to the tube and a knife blade and, by heat dissipation, to the environment;

a thermally conductive metal knife blade having a rear end cylindrical receptacle adapted to receive a shaft of said enclosure tube in heat transfer adjacency to create a heat transfer interface between the heating element, enclosure tube, heat sink body, and knife blade that maintains the temperature range at a tip of the blade within a temperature range of about ±50 degrees Fahrenheit from a selected temperature for searing or cutting thermoplastic dental trays without a need to adjust the input power level to said heating element.

2. The knife of claim 1 wherein said heatsink body is a collar on the enclosure tube.

3. The knife of claim 1 wherein:

each winding of the element is in continuous and in uniform contact with each adjacent winding and each winding of the element is in continuous uniform contact with the ceramic tube core and the resistive wire is in a thermally communicative relationship with said enclosure tube, whereby heat is transferred by radiation and convection from the winding element to the inner surface of the enclosure tube.

4. The knife of claim 1, wherein the resistive wire of the element has a diameter within the range of from about 0.2 mm to about 0.3 mm.

5. The knife of claim 1, wherein the ceramic tubular core has an outer diameter within the range of from about 1.5 to about 2.5 mm; and an inner diameter from about 0.5 mm to about 1.5 mm.

6. The knife claim 1, wherein the heating element enclosure tube has an inner diameter within the range of from about 3.5 mm to about 5.5 mm;

an outer diameter within the range of from about 4.1 mm to about 6.1 mm; and a stainless steel structure.

7. The knife of claim 1, wherein the heat sink body comprises:

a notched minimum outer diameter within the range of from about 4.12 mm to about 5.12 mm;

a set of outwardly stepped outermost outer diameters within the range of from about 8 mm to about 12 mm;

an innermost diameter with the range of from about 4.1 mm to about 6.5 mm a stainless steel structure; and having a heat transfer gradient which stabilizes the heat transfer to the knife blade and stabilizes heat dissipation to the environment thereby maintaining a temperature range of about ±50 degrees Fahrenheit at the knife blade tip.

8. A heated dental knife for trimming thermoplastic dental trays, comprising:

a handle having a textured gripping area and an opening therein;

a blade which extends beyond the handle opening for a distance within the range of from about 25 mm to about 60 mm and which includes a double-edged straight-sided chevron blade tip in the horizontal direction, providing bi-directional cutting edges;

a heater; and a concave taper blade tip in the vertical direction, thereby resulting in an ergonomically designed knife blade.

9. The knife claim 7, wherein the blade tip has a concave taper in the vertical direction within the range of about from 3 mm to about 0.25 mm over the last 20% of the length of the knife blade on the tip end to form a sharp point, thereby optimizing the cutting edge for trimming thermoplastic dental trays while formed on a dental model.

10. The double edged blade tip of claim 7, wherein:

the chevron tip has an angle within the range of from about 30 to about 50 degrees for ease of maneuvering blade between teeth.

11. The knife blade of claim 7, wherein:

the blade extends for a distance within the range of from about 40 mm beyond the handle opening to about 50 mm in length.

* * * * *